United States Patent [19]
Hollis et al.

[11] Patent Number: 5,629,415
[45] Date of Patent: May 13, 1997

[54] DNA ENCODING CANINE IMMUNOGLOBULIN E

[75] Inventors: Gregory F. Hollis, Westfield; Mayur D. Patel, Edison, both of N.J.

[73] Assignee: Merck & Co., Inc., Rahway, N.J.

[21] Appl. No.: 336,583

[22] Filed: Nov. 9, 1994

[51] Int. Cl.$^6$ .................................................. C07H 21/00
[52] U.S. Cl. .................................. 536/23.53; 435/172.3; 435/320.1; 530/387.1; 530/388.1
[58] Field of Search .............................. 424/130.1, 805; 435/69.6, 172.3, 240.27, 320.1; 530/387.1, 862, 388.1; 536/23.53; 935/15

[56] References Cited

FOREIGN PATENT DOCUMENTS

WO94/21676  9/1994  WIPO .......................... C07K 7/10

OTHER PUBLICATIONS

Burgess et al., J. of Cell. Biology, 111:2129–2138, 1990.
Lazar et al., Molec. and Cell. Biol., 8(3):1247–1253, (1988).
Tao et al., J. of Immunol., 143(8):2595–2601, 1989.

*Primary Examiner*—Toni R. Scheiner
*Attorney, Agent, or Firm*—Christine E. Carty; Jack L. Tribble

[57] ABSTRACT

The present invention relates to DNA molecules encoding a canine IgE and species-specific regions of the canine IgE constant region. The invention comprises the DNA molecules, proteins encoded by the DNA molecules, antibodies to the proteins, cells transformed by the DNA molecules, assays employing the transformed cells, compounds identified by the assays and kits containing the DNA molecules or derivatives thereof.

4 Claims, 5 Drawing Sheets

```
      10              30              50
       .               .               .
  1  CAGAGCAGATACCCAGGTCAACAGCGGGCCTGGCATATGATGGGGTGACAGTCCCCAAGG  60

70              90              110
       .               .               .
 61  CAGGCACTGACACTGGCCCTGTCCCCACAGCCACCAGCCAGGACCTGTCTGTGTTCCCCT  120
                                  XXThrSerGlnAspLeuSerValPheProL 130             150             170
       .               .               .
121  TGGCCTCCTGCTGTAAAGACAACATCGCCAGTACCTCTGTTACACTGGGCTGTCTGGTCA  180
     euAlaSerCysCysLysAspAsnIleAlaSerThrSerValThrLeuGlyCysLeuValT 190             210             230
       .               .               .
181  CCGGCTATCTCCCCATGTCGACAACTGTGACCTGGGACACGGGGTCTCTAAATAAGAATG  240
     hrGlyTyrLeuProMetSerThrThrValThrTrpAspThrGlySerLeuAsnLysAsnV 250             270             290
       .               .               .
241  TCACGACCTTCCCCACCACCTTCCACGAGACCTACGGCCTCCACAGCATCGTCAGCCAGG  300
     alThrThrPheProThrThrPheHisGluThrTyrGlyLeuHisSerIleValSerGlnV 310             330             350
       .               .               .
301  TGACCGCCTCGGGCAAGTGGGCCAAACAGAGGTTCACCTGCAGCGTGGCTCACGCTGAGT  360
     alThrAlaSerGlyLysTrpAlaLysGlnArgPheThrCysSerValAlaHisAlaGluS 370             390             410
       .               .               .
361  CCACCGCCATCAACAAGACCTTCAGTGGTAAGCCAGGGTTGGGCTGGCCCACATGACACT  420
     erThrAlaIleAsnLysThrPheSerA 430             450             470
       .               .               .
421  GGAGGGAGAAGGGACAGGCTGGGCGGGAGTGGTAGGAGAGGGGTGGTGGGCGGGCCCGAA  480

490             510             530
       .               .               .
481  TGCCGCCATGGCTGGTAACGCCCAGCACATGTGGGGCTGGGGCTGACACATGAGTCCCGT  540
```

FIG.1A

```
                550                  570                  590
541  GGGCTCAGAGACACCACTGCCACATGGCTGCCTCTACTTCTAGCATGTGCCTTAAACTTC  600
                                                laCysAlaLeuAsnPhe 610                  630                  650
601  ATTCCGCCTACCGTGAAGCTCTTCCACTCCTCCTGCAACCCCGTCGGTGATACCCACACC  660
     IleProProThrValLysLeuPheHisSerSerCysAsnProValGlyAspThrHisThr 670                  690                  710
661  ACCATCCAGCTCCTGTGCCTCATCTCTGGCTACGTCCCAGGTGACATGGAGGTCATCTGG  720
     ThrIleGlnLeuLeuCysLeuIleSerGlyTyrValProGlyAspMetGluValIleTrp 730                  750                  770
721  CTGGTGGATGGGCAAAAGGCTACAAACATATTCCCATACACTGCACCCGGCACAAAGGAG  780
     LeuValAspGlyGlnLysAlaThrAsnIlePheProTyrThrAlaProGlyThrLysGlu 790                  810                  830
781  GGCAACGTGACCTCTACCCACAGCGAGCTCAACATCACCCAGGGCGAGTGGGTATCCCAA  840
     GlyAsnValThrSerThrHisSerGluLeuAsnIleThrGlnGlyGluTrpValSerGln 850                  870                  890
841  AAAACCTACACCTGCCAGGTCACCTATCAAGGCTTTACCTTTAAAGATGAGGCTCGCAAG  900
     LysThrTyrThrCysGlnValThrTyrGlnGlyPheThrPheLysAspGluAlaArgLys 910                  930                  950
901  TGCTCAGGTATGGCCCCCCTGTCCCCCAGAAACCCAGATGCGCGAGGCTCAGAGATGAGG  960
     CysSerG 970                  990                  1010
961  GCCAAGGCACGCCCTCATGCAGCCTCTCACACACTGCAGAGTCCGACCCCCGAGGCGTGA 1020
                                            luSerAspProArgGlyValT
```

FIG. 1B

```
                    1030              1050              1070
1021  CGAGCTACCTGAGCCCACCCAGCCCCCTTGACCTGTATGTCCACAAGGCGCCCAAGATCA  1080
      hrSerTyrLeuSerProProSerProLeuAspLeuTyrValHisLysAlaProLysIleT 1090              1110              1130
1081  CCTGCCTGGTAGTGGACCTGGCCACCATGGAAGGCATGAACCTGACCTGGTACCGGGAGA  1140
      hrCysLeuValValAspLeuAlaThrMetGluGlyMetAsnLeuThrTrpTyrArgGluS 1150              1170              1190
1141  GCAAAGAACCCGTGAACCCGGGCCCTTTGAACAAGAAGGATCACTTCAATGGGACGATCA  1200
      erLysGluProValAsnProGlyProLeuAsnLysLysAspHisPheAsnGlyThrIleT 1210              1230              1250
1201  CAGTCACGTCTACCCTGCCAGTGAACACCAATGACTGGATCGAGGGCGAGACCTACTATT  1260
      hrValThrSerThrLeuProValAsnThrAsnAspTrpIleGluGlyGluThrTyrTyrC 1270              1290              1310
1261  GCAGGGTGACCCACCCGCACCTGCCCAAGGACATCGTGCGCTCCATTGCCAAGGCCCCTG  1320
      ysArgValThrHisProHisLeuProLysAspIleValArgSerIleAlaLysAlaProG 1330              1350              1370
1321  GTGAGCCACGGGCCCAGGGGAGGTGGGCGGGCCTCCTGAGCCGGAGCCTGGGCTGACCCC  1380

1390              1410              1430
1381  ACACCTATCCACAGGCAAGCGTGCCCCCCGGATGTGTACTTGTTCCTGCCACCGGAGGA  1440
                    lyLysArgAlaProProAspValTyrLeuPheLeuProProGluGl 1450              1470              1490
1441  GGAGCAGGGGACCAAGGACAGAGTCACCCTCACGTGCCTGATCCAGAACTTCTTCCCCGC  1500
      uGluGlnGlyThrLysAspArgValThrLeuThrCysLeuIleGlnAsnPhePheProAl
```

FIG.1C

```
              1510                1530                1550
               .                   .                   .
1501  GGACATTTCAGTGCAATGGCTGCGAAACGACAGCCCCATCCAGACAGACCAGTACACCAC  1560
      aAspIleSerValGlnTrpLeuArgAsnAspSerProIleGlnThrAspGlnTyrThrTh 1570                1590                1610
               .                   .                   .
1561  CACGGGGCCCCACAAGGTCTCGGGCTCCAGGCCTGCCTTCTTCATCTTCAGCCGCCTGGA  1620
      rThrGlyProHisLysValSerGlySerArgProAlaPhePheIlePheSerArgLeuGl 1630                1650                1670
               .                   .                   .
1621  GGTTAGCCGGGTGGACTGGGAGCAGAAAAACAAATTCACCTGCCAAGTGGTGCATGAGGC  1680
      uValSerArgValAspTrpGluGlnLysAsnLysPheThrCysGlnValValHisGluAl 1690                1710                1730
               .                   .                   .
1681  GCTGTCCGGCTCTAGGATCCTCCAGAAATGGGTGTCCAAAACCCCCGGTAAATGATGCCC  1740
      aLeuSerglySerArgIleLeuGlnLysTrpValSerLysThrProGlyLys 1750                1770                1790
               .                   .                   .
1741  ACCCTCCTCCCGCCGCCACCCCCCAGGGCTCCACCTGCTGGGAGGGAGGGGGGCTGGCAA  1800

1810                1830                1850
               .                   .                   .
1801  GACCCTCCATCTGTCCTTGTCAATAAACACTCCAGTGTCTGCTTGGAGCCCTGGGCACAC  1860

1870                1890                1910
               .                   .                   .
1861  CCATTTCTTGGGGGTGGGCAGGGTTGCAGAGCAGGGATGTCTTGGCACAGAAGGGTCCCC  1920

1921  CAGGGTGT  1928
```

FIG. 1D

| % IDENTITY OF CANINE Igε TO Igε OF OTHER SPECIES | | | | | |
|---|---|---|---|---|---|
| | CH1 | CH2 | CH3 | CH4 | TOTAL |
| MOUSE Igε DNA | 54 | 63 | 64 | 66 | 62 |
| MOUSE Igε PROTEIN | 42 | 42 | 55 | 56 | 49 |
| HUMAN Igε DNA | 69 | 67 | 74 | 71 | 70 |
| HUMAN Igε PROTEIN | 59 | 53 | 62 | 55 | 57 |

FIG.2

DNA ENCODING CANINE IMMUNOGLOBULIN E

BACKGROUND OF THE INVENTION

This invention describes cloning and characterization of the canine IgE gene. The canine IgE gene was isolated using a human IgA constant region probe to clone a piece of the dog genome. IgA-containing cloned fragments of the dog genome were searched for IgE-related sequences. The identified areas were characterized in detail by nucleotide sequence analysis. This invention provides specific sequence information which permits targeted modulation of IgE-mediated immune responses.

The invention relates to DNA molecules encoding a canine IgE and species specific regions of canine IgE constant region. The invention comprises the DNA molecules, proteins encoded by the DNA molecules, antibodies to the proteins, cells transformed by the DNA molecules, assays employing the transformed cells, compounds identified by the assays and kits containing the DNA molecules or derivatives thereof.

Traditionally, hypersensitivity responses in the dog have been controlled by corticosteroid therapy which has adverse metabolic effects and produces generalized immunosuppression. The cloning and sequence determination of the canine IgE gene permits novel approaches to the control of IgE-mediated hypersensitivity reactions by facilitating targeting of the IgE molecule and its interaction with the IgE receptor. These approaches include, but are not limited to eliciting an immune response directed at specific peptide epitopes present in canine IgE to control allergic reactions and using the canine IgE sequence as pan of a screen to identify small molecules that alter IgE mediated responses to allergens.

Immunoglobulin (Ig) proteins consist of two identical light (L) chains and two identical heavy (H) chains. Both Ig L and H chains contain an amino-terminal variable region of approximately 110 amino acids that forms the antigen binding domain. The carboxy terminal constant (C) region domains of each chain is defined by two isotypes of IgL chain (kappa and lambda) and multiple isotypes of IgH chains ( mu, delta, gamma, epsilon and alpha which define IgM, IgD, IgG, IgE, and IgA, respectively). The IgH chain C regions contain the effector functions common to antibodies of a given isotype.

IgE antibodies are responsible for mediating allergic responses. IgE binds to mast cells through an Fce receptor and, when cross-linked by binding antigen, triggers a cascade of events-that leads to the release of allergic mediators. Because of the central role that IgE plays in mediating allergic reactions, the region of the Ige constant region involved in Fce receptor binding is of great interest. Inhibition of binding of IgE to its receptor on mast cells may be a way to control allergic responses.

Interestingly, of all five isotypes of immunoglobulin, the sequence of the Ige C region is the least well conserved across species. Consequently, studies of allergic reactions in a specific species are aided by having the primary amino acid sequence available for the Ige C region gene of that species.

The IgE antibody class plays a central role in type I immediate hypersensitivity. IgE binds to specific high-affinity receptors on mast cells and basophils and, when associated with antigen, triggers degranulation of vasoactive substances to produce allergic reactions. Because of its role in allergy, substantial effort has been made to understand how the Ige C region (which defines IgE) interacts with the Fcα receptor on mast cells and basophils to trigger degranulation upon binding antigen. These studies indicate that binding to the Fce receptor reside in the Ige CH3 and CH4 domains. Additional studies have used linear peptides to map the Ige binding site. In one of these studies, an octapeptide from the human Ige gene (Pro345-Phe-Asp-Leu-Phe-Ile-Arg-Lys352) inhibited passive sensitization, presumably by occupying the Fce receptor sites on cells (Nio et. al. 1993). The equivalent region of the canine Ige chain shares only 50% identity with this octapeptide (Canine sequence: Pro-Leu-Asp-Leu-Tyr-Val-His-Lys). Based on this observation, attempts to use IgE peptides involved in Fce receptor binding to modulate allergic reactions in dogs would require the use of peptides derived from the canine Ige sequence.

The sequences of the IgE constant regions from several species including human, rat and mouse have been reported. Peptides derived from known IgE sequences have been used to generate antibodies which alter IgE function. U.S. Pat. No. 5,091,313 is directed to the prevention or control of IgE-mediated allergic symptoms through the use of monoclonal or polyclonal antibodies raised against epitopes present in B cell-associated or soluble human IgE. WO90/15878 discloses the use of peptides derived from human, rat or mouse IgE sequences to generate antibodies which inhibit IgE-mediated mast cell degranulation. U.S. Pat. No. 4,223,016 discloses the use of peptides derived from IgE sequences for allergic desensitization.

The present invention identifies a species-specific sequence is of the canine IgE constant region. For therapeutic purposes, it may be desirable to generate antibodies against the IgE of the target species in order to maximize the affinity of the anti-IgE antibodies. In addition, screening assays aimed at the identification of small molecules which alter IgE mediated responses in the dog can be optimized through the use of canine IgE, the actual target.

Prior to the described invention, it was virtually impossible to design peptides which could be used to produce antibodies of specifically targeted against canine IgE. When IgE sequences from other species are used for this purpose, the resulting antibodies have reduced affinity for the canine IgE and, therefore, reduced efficacy compared with antibodies generated using the described invention. Further, the availability of the cloned canine IgE gene enables large quantities of the canine IgE protein to be produced recombinantly for use in drug development (e.g., small molecule screening, assay development and anti-IgE antibody generation).

The DNA of the present invention may be used to identify regions of the canine IgE which are homologous to those targeted in other species and to predict novel therapeutic targets. Therapeutically interesting portions of the sequence mad be expressed in chimeric proteins or used to produce peptides. These molecules or conjugate derivatives thereof may then be used, with or without adjuvants, as canine vaccines to treat or prevent IgE mediated-hypersensitivity responses. Alternately, the derived peptides or proteins may be used to produce monoclonal or polyclonal antibodies for passive treatment of IgE-mediated hypersensitivity.

The invention also provides a renewable source of canine IgE protein through its expression using recombinant DNA techniques. This provides material for establishing assays to monitor IgE-mediated immune responses as well as for developing screens to identify small molecules capable of disrupting IgE-mediated allergic reactions in the dog.

BRIEF DESCRIPTION OF THE DRAWINGS

FIG. 1 shows the nucleotide and predicted amino acid sequences of canine immunoglobulin E.

FIG. 2 shows a comparison of percent identity of nucleotide and amino acid sequence of canine IgE chain to human and mouse IgE chain.

SUMMARY OF THE INVENTION

The present invention relates to DNA molecules encoding a canine IgE and species-specific regions of the canine IgE constant region. The invention comprises the DNA molecules, proteins encoded by the DNA molecules, antibodies to the proteins, cells transformed by the DNA molecules, assays employing the transformed cells, compounds identified by the assays and kits containing the DNA molecules or derivatives thereof.

Detailed Description of the Invention

The present invention relates to DNA molecules encoding a canine IgE and species-specific regions of the canine IgE constant region. The invention comprises the DNA molecules, proteins encoded by the DNA molecules, antibodies to the proteins, cells transformed by the DNA molecules, assays employing the transformed cells, compounds identified by the assays and kits containing the DNA molecules or derivatives thereof.

DNA encoding canine IgE from a particular species of canine may be used to isolate and purify homologues of canine IgE from other canines. To accomplish this, the first canine IgE DNA may be mixed with a sample containing DNA encoding homologues of canine IgE under appropriate hybridization conditions. The hybridized DNA complex may be isolated and the DNA encoding the homologous DNA may be purified therefrom.

It is known that there is a substantial amount of redundancy in the various codons which code for specific amino acids. Therefore, this invention is also directed to those DNA sequences which contain alterative codons which code for the eventual translation of the identical amino acid. For purposes of this specification, a sequence bearing one or more replaced codons will be defined as a degenerate variation. Also included within the scope of this invention are mutations either in the DNA sequence or the translated protein which do not substantially alter the ultimate physical properties of the expressed protein. For example, substitution of valine for leucine, arginine for lysine, or asparagine for glutamine may not cause a change in functionality of the polypeptide.

It is known that DNA sequences coding for a peptide may be altered so as to code for a peptide having properties that are different than those of the naturally-occurring peptide. Methods of altering the DNA sequences include, but are not limited to site directed mutagenesis.

As used herein, a "functional derivative" of canine IgE is a compound that possesses a biological activity (either functional or structural) that is substantially similar to the biological activity of canine IgE. The term "functional derivatives" is intended to include the "fragments," "variants," "degenerate, variants," "analogs" and "homologues" or to "chemical derivatives" of canine IgE. The term "fragment" is meant to refer to any polypeptide subset of canine IgE. The term "variant" is meant to refer to a molecule substantially similar in structure and function to either the entire canine IgE molecule or to a fragment thereof. A molecule is "substantially similar" to canine IgE if both molecules have substantially similar structures or if both molecules possess similar biological activity. Therefore, if the two molecules possess substantially similar activity, they are considered to be variants even if the structure of one of the molecules is not found in the other or even if the two amino acid sequences are not identical. The term "analog" refers to a molecule substantially similar in function to either the entire canine IgE molecule or to a fragment thereof.

As used herein, a protein or peptide is "substantially pure" when that protein or peptide has been purified to the extent that it is essentially free of other molecules with which it is associated in nature. The term "substantially pure" is used relative to proteins or peptides with which the peptides of the instant invention are associated in nature, and are not intended to exclude compositions in which the peptide of the invention is admixed with nonproteinous pharmaceutical carriers or vehicles.

As used herein, an amino acid sequence substantially homologous to a referent IgE protein will have at least 70% sequence homology, preferably 80%, and most preferably 90% sequence homology with the amino acid sequence of a referent IgE protein or a peptide thereof. For example, an amino, acid sequence is substantially homologous to canine IgE protein if, when aligned with canine IgE protein, at least 70% of its amino acid residues are the same.

As used herein, a DNA sequence substantially homologous to a referent canine IgE protein will have at least 70%, preferably 80%, and most preferably 90% sequence homology with the DNA sequence of a referent canine IgE. Moreover, a DNA sequence substantially homologous to a referent canine IgE protein is characterized by the ability to hybridize to the DNA sequence of a referent canine IgE under standard conditions. Standard hybridization conditions are described in Maniatis, T., et al. (1989) Molecular Cloning, Cold Spring Harbor Laboratory, Cold Spring Harbor, N.Y.

A variety of procedures known in the an may be used to molecularly clone canine IgE DNA. These methods include, but are not limited to, direct functional expression of the canine IgE genes following the construction of a canine IgE-containing cDNA or genomic DNA library in an appropriate. expression vector system. Another method is to screen canine IgE-containing cDNA or genomic DNA library constructed in a bacteriophage or plasmid shuttle vector with a labeled oligonucleotide probe designed from the amino acid sequence of the canine IgE subunits. An additional method consists of screening a canine IgE-containing cDNA or genomic DNA libraries constructed in a bacteriophage or plasmid shuttle vector with a partial DNA encoding the canine IgE. This partial DNA is obtained by the specific PCR amplification of canine IgE DNA fragments through the design of degenerate oligonucleotide primers from the amino acid sequence of the purified canine IgE. Another method is to isolate RNA from canine IgE-producing cells and translate the RNA into protein via an in vitro or an in vivo translation system. The translation of the RNA into a peptide or a protein will result in the production of at least a portion of the canine IgE protein which can be identified by, for example, by the activity of canine IgE protein or by immunological reactivity with an anti-canine IgE antibody. In this method, pools of s RNA isolated from canine IgE-producing cells can be analyzed for the presence of an RNA which encodes at least a portion of the canine IgE protein. Further fractionation of the RNA pool can be done to purify the canine IgE RNA from non-canine IgE RNA. The peptide or protein produced by this method may be analyzed to provide amino acid sequences which in turn are used to provide primers for production of canine IgE cDNA, or the RNA used for translation can be analyzed to provide nucleotide sequences encoding canine IgE and produce probes for the production of canine IgE cDNA. These methods are known in the art and can be found in, for example, Sambrook, J., Fritsch, E. F., Maniatis, T. in Molecular Cloning: A Laboratory Manual, Second Edition, Cold Spring Harbor Laboratory Press, Cold Spring Harbor, N.Y. 1989.

Other types of libraries, as well as libraries constructed from other cells or cell types, may be useful for isolating canine IgE-encoding DNA. Other types of libraries include, but are not limited to, cDNA libraries derived from other canines or cell lines derived from other canines, and genomic DNA libraries.

Preparation of cDNA libraries can be performed by standard techniques. Well known cDNA library construction techniques can be found in, for example, Sambrook, J., et al., supra.

DNA encoding canine IgE may also be isolated from a suitable genomic DNA library. Construction of genomic DNA libraries can be performed by standard techniques. Well known genomic DNA library construction techniques can be found in Sambrook, J., et al, supra In order to clone the canine IgE gene by the above methods, knowledge of the amino acid sequence of canine IgE may be necessary. To accomplish this, canine IgE protein may be purified and partial amino acid sequence determined by manual sequencing or automated sequence. It is not necessary to determine the entire amino acid sequence, but the linear sequence of two regions of 6 to 8 amino acids from the protein is determined for the production of primers for PCR amplification of a partial canine IgE DNA fragment.

Once suitable amino acid sequences have been identified, the DNA sequences capable of encoding them are synthesized. Because the genetic code is degenerate, more than one codon may be used to encode a particular amino acid., and therefore, the amino acid sequence can be encoded by any of a set of similar DNA oligonucleotides. Only one member of the set will be identical to the canine IgE sequence but will be capable of hybridizing to canine IgE DNA even in the presence of DNA oligonucleotides with mismatches under appropriate conditions. Under alternate conditions, the mismatched DNA oligonucleotides may still sufficiently hybridize to the canine IgE DNA to permit identification and isolation of canine IgE encoding DNA.

Purified biologically active canine IgE may have several different physical forms. Canine IgE may exist as a full-length nascent or unprocessed polypeptide, or as partially processed polypeptides or combinations of processed polypeptides. The full-length nascent canine IgE polypeptide may be postranslationally modified by specific proteolytic cleavage events which result in the formation of fragments of the full length nascent polypeptide.

Canine IgE in substantially pure form derived from natural sources or from recombinant host cells according to the purification processes described herein, is found to be a polypeptide encoded by a single mRNA.

The cloned canine IgE DNA obtained through the methods described herein may be recombinantly expressed by molecular cloning into an expression vector containing a suitable promoter and other appropriate transcription regulatory elements, and transferred into prokaryotic or eukaryotic host cells to produce recombinant canine IgE. Techniques for such manipulations are fully described in Sambrook, J., et al., supra.

Expression vectors are defined herein as DNA sequences that are required for the transcription of cloned copies of genes and the translation of their mRNAs in an appropriate host. Such vectors can be used to express eukaryotic genes in a variety of hosts such as bacteria, bluegreen algae, plant cells, insect cells, fungal cells and animal cells.

Specifically designed vectors allow the shuttling of DNA between hosts such as bacteria-yeast or bacteria-animal cells or bacteria-fungal cells or bacteria-invertebrate cells. An appropriately constructed expression vector should contain: an origin of replication for autonomous replication in host cells, selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one which causes mRNAs to be initiated at high frequency. Expression vectors may include, but are not limited to, cloning vectors, modified cloning vectors, specifically designed plasmids or viruses.

A variety of mammalian expression vectors may be used to express recombinant canine IgE in mammalian cells. Commercially available mammalian expression vectors which may be suitable for recombinant canine IgE expression, include but are not limited to, pcDNA3 (Invitrogen), pMC1neo (Stratagene), pXT1 (Stratagene), pSG5 (Stratagene), EBO-pSV2-neo (ATCC 37593) pBPV-1(8-2) (ATCC 37110), pdBPV-MMTneo(342-12) (ATCC 37224), pRSVgpt (ATCC 37199), pRSVneo (ATCC 37198), pSV2-dhfr (ATCC 37146), pUCTag (ATCC 37460), and λZD35 (ATCC 37565).

A variety of bacterial expression vectors may be used to express recombinant canine IgE in bacterial cells. Commercially available bacterial expression vectors which may be suitable for recombinant canine IgE expression include, but are not limited to pET11a (Novagen), lambda gt11 (Invitrogen), pcDNAII (Invitrogen), pKK223-3 (Pharmacia).

A variety of fungal cell expression vectors may be used to express recombinant canine IgE in fungal cells. Commercially available fungal cell expression vectors which may be suitable for recombinant canine IgE expression include but are not limited to pYES2 (Invitrogen), Pichia expression vector (Invitrogen).

A variety of insect cell expression vectors may be used to express recombinant canine. IgE in insect cells. Commercially available insect cell expression vectors which may be suitable for recombinant expression of canine IgE include but are not limited to pBlue Bac HIII (Invitrogen).

An expression vector containing DNA encoding canine IgE may be used for expression of canine IgE in a recombinant host cell. Recombinant host cells may be prokaryotic or eukaryotic, including but not limited to bacteria such as E. coli, fungal cells such as yeast, mammalian cells including but not limited to cell lines of human, bovine, porcine, monkey and rodent origin, and insect cells including but not limited to Drosophila and silkworm derived cell lines. Cell lines derived from mammalian species which may be suitable and which are commercially available, include but are not limited to, L cells L-M(TK⁻) (ATCC CCL 1.3), L cells L-M (ATCC CCL 1.2), 293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL, 2), C127I (ATCC CRL 1616), BS-C-1 (ATCC CCL 26) and MRC-5 (ATCC CCL 171).

The expression vector may be introduced into host cells via any one of a number of techniques including but not limited to transformation, transfection, lipofection, protoplast fusion, and electroporation. The expression vector-containing cells are clonally propagated and individually analyzed to determine whether they produce canine IgE protein. Identification of canine IgE expressing host cell clones may be done by several means, including but not limited to immunological reactivity with anti-canine IgE antibodies, and the presence of host cell-associated canine IgE activity, such as canine IgE-specific ligand binding or signal transduction defined as a response mediated by the interaction of canine IgE-specific ligands at the receptor.

Expression of canine IgE DNA may also be performed using in vitro produced synthetic mRNA or native mRNA. Synthetic mRNA or mRNA isolated from canine IgE producing cells can be efficiently translated in various cell-free systems, including but not limited to wheat germ extracts and reticulocyte extracts, as well as efficiently translated in cell-based systems, including but not limited to microinjection into frog oocytes, with microinjection into frog oocytes being preferred.

Host cell transfectants and microinjected oocytes may be assayed for both the levels of canine IgE receptor activity and levels of canine IgE protein by a variety of methods.

Following expression of canine IgE in a recombinant host cell, canine IgE protein may be recovered to provide canine IgE in purified form. Several canine IgE purification procedures are available and suitable for use. As described herein, recombinant canine IgE may be purified frown cell lysates and extracts by various combinations of, or individual application of salt fractionation, ion exchange chromatography, size exclusion chromatography, hydroxylapatite adsorption chromatography and hydrophobic interaction chromatography.

In addition, recombinant canine IgE can be separated from other cellular proteins by use of an immunoaffinity column made with monoclonal or polyclonal antibodies specific for full length nascent canine IgE, or polypeptide fragments of canine IgE.

Monospecific antibodies to canine IgE are purified from mammalian antisera containing antibodies reactive against canine IgE or are prepared as monoclonal antibodies reactive with canine IgE using the technique of Kohler and Milstein, Nature 256, 495–497 (1975). Monospecific antibody as used herein is defined as a single antibody species or multiple antibody species with homogenous binding characteristics for canine IgE. Homogenous binding as used herein refers to the ability of the antibody species to bind to a specific antigen or epitope, such as those associated with the canine IgE, as described above. Canine IgE specific antibodies are raised by immunizing animals such as mice, rats, guinea pigs, rabbits, goats, horses and the like, with rabbits being preferred, with an appropriate concentration of canine IgE, either with or without an immune adjuvant.

Monoclonal antibodies (mAb) reactive with canine IgE are prepared by immunizing inbred mice, preferably Balb/c, with canine IgE. The mice are immunized by the IP or SC route with about 0.1 µg to about 10 µg, preferably about 1 µg, of canine IgE in about 0.5 ml buffer or saline incorporated in an equal volume of an acceptable adjuvant, as discussed above. Freund's complete adjuvant is preferred. The mice receive an initial immunization on day 0 and are rested for about 3 to about 30 weeks. Immunized mice are given one or more booster immunizations of about 0.1 to about 10 µg of canine IgE in a buffer solution such as phosphate buffered saline by the intravenous (IV) route. Lymphocytes, from antibody positive mice, preferably splenic lymphocytes, are obtained by removing spleens from immunized mice by standard procedures known in the art. Hybridoma cells are produced by mixing the splenic lymphocytes with an appropriate fusion partner, preferably myeloma cells, under conditions which will allow the formation of stable hybridomas. Fusion partners may include, but are not limited to: mouse myelomas P3/ NS1/ Ag 4–1; MPC-11; S-194 and Sp 2/0, with Sp 2/0 being preferred. The antibody producing cells and myeloma cells are fused in polyethylene glycol, about 1000 molecular weight, at concentrations from about 30% to about 50%. Fused hybridoma cells are selected by growth in hypoxanthine, thymidine and aminopterin supplemented Dulbecco's modified Eagles Medium (DMEM) by procedures known in the art. Supernatant fluids are collected from growth positive wells on about days 14, 18, and 21 and are screened for antibody production by an immunoassay such as solid phase immunoradioassay (SPIRA) using canine IgE as the antigen. The culture fluids are also tested in the Ouchterlony precipitation assay to determine the isotype of the mAb. Hybridoma cells from antibody positive wells are cloned by a technique such as the soft agar technique of MacPherson. Soft Agar Techniques, in *Tissue Culture Methods and Applications*, Kruse and Paterson, Eds., Academic Press, 1973.

Monoclonal antibodies are produced in vivo by injection of pristane primed Balb/c mice, approximately 0.5 ml per mouse, with about $2 \times 10^6$ to about $6 \times 10^6$ hybridoma cells about 4 days after priming. Ascites fluid is collected at approximately 8–12 days after cell transfer and the monoclonal antibodies are purified by techniques known in the art.

In vitro production of anti-canine IgE mAb is carried out by growing the hydridoma in DMEM containing about 2% fetal calf serum to obtain sufficient quantities of the specific mAb. The mAb are purified by techniques known in the art.

Antibody tilers of ascites or hybridoma culture fluids are determined by various serological or immunological assays which include, but are not limited to, precipitation, passive agglutination, enzyme-linked immunosorbent antibody (ELISA) technique and radioimmunoassay (RIA) techniques. Similar assays are used to detect the presence of canine IgE in body fluids or tissue and cell extracts.

The above described methods for producing monospecific antibodies may be utilized to produce antibodies specific for canine IgE polypeptide fragments, or full-length nascent canine IgE polypeptide The present invention is also directed to methods for screening for compounds which modulate the expression of DNA or RNA encoding canine IgE as well as the function of canine IgE protein in vivo. Compounds which modulate these activities may be DNA, RNA, peptides, proteins, or non-proteinaceous organic molecules. Compounds may modulate by increasing or attenuating the expression of DNA or RNA encoding canine IgE, or the function s of canine IgE protein. Compounds that modulate the expression of DNA or RNA encoding canine IgE or the function of canine IgE protein may be detected by a variety of assays. The assay may be a simple "yes/no" assay to determine whether there is a change in expression or function. The assay may be made quantitative by comparing the expression or function of a test sample with the levels of expression or function in a standard sample.

Kits containing canine IgE DNA, antibodies to canine IgE, or canine IgE protein may be prepared. Such kits are used to detect DNA which hybridizes to canine IgE DNA or to detect the presence of canine IgE protein or peptide fragments in a sample. Such characterization is useful for a variety of purposes including but not limited to forensic analyses and epidemiological studies.

The DNA molecules, RNA molecules, recombinant protein and antibodies of the present invention may be used to screen and measure levels of canine IgE DNA, canine IgE RNA or canine IgE protein. The recombinant proteins, DNA molecules, RNA molecules and antibodies lend themselves to the formulation of kits suitable for the detection and typing of canine IgE. Such a kit would comprise a compartmentalized carrier suitable to hold in close confinement at least one container. The carrier would further comprise reagents such as recombinant canine IgE protein or anticanine IgE antibodies suitable for detecting canine IgE. The carrier may also contain a means for detection :such as labeled antigen or enzyme substrates or the like.

Nucleotide sequences that are complementary to the canine IgE encoding DNA sequence can be synthesized for antisense therapy. These antisense molecules may be DNA, stable derivatives of DNA such as phosphorothioates or methylphosphonates, RNA, stable derivatives of RNA such as 2'-O-alkylRNA, or other canine IgE antisense oligonucleotide mimetics. canine IgE antisense molecules may be introduced into cells by microinjection, liposome encapsulation or by expression from vectors harboring the antisense sequence. canine IgE antisense therapy may be particularly useful for the treatment of diseases where it is beneficial to reduce canine IgE activity.

Pharmaceutically useful compositions comprising canine IgE DNA, canine IgE RNA, or canine IgE protein, or modulators of canine IgE activity, may be formulated according to known methods such as by the admixture of a pharmaceutically acceptable carder. Examples of such carders and methods of formulation may be found in Remington's Pharmaceutical Sciences. To form a pharmaceutically acceptable composition suitable for effective administration, such compositions will contain an effective amount of the protein, DNA, RNA, or modulator.

Therapeutic or diagnostic compositions of the invention are administered to an individual in amounts sufficient to treat or diagnose canine IgE related disorders. The effective amount may vary according to a variety of factors such as the animal's condition, weight, sex and age. Other factors include the mode of administration.

The pharmaceutical compositions may be provided to the animal by a variety of routes such as subcutaneous, topical, oral and intramuscular.

The term "chemical derivative" describes a molecule that contains additional chemical moieties which are not normally a part of the base molecule. Such moieties may improve the solubility, half-life, absorption, etc. of the base molecule. Alternatively the moieties may attenuate undesirable side effects of the base molecule or decrease the toxicity of the base molecule. Examples of such moieties are described in a variety of texts, such as Remington's Pharmaceutical Sciences.

Compounds identified according to the methods disclosed herein may be used alone at appropriate dosages defined by routine testing in order to obtain optimal inhibition of the canine IgE or its activity while minimizing any potential toxicity. In addition, coadministration or sequential administration of other agents may be desirable.

The present invention also has the objective of providing suitable topical, oral, systemic and parenteral pharmaceutical formulations for use in the methods of treatment of the present invention. The compositions containing compounds identified according to this invention as the active ingredient for use in the modulation of canine IgE can be administered in a wide variety of therapeutic dosage forms in conventional vehicles for administration. For example, the compounds can be administered in such oral dosage forms as tablets, capsules (each including timed release and sustained release formulations), pills, powders, granules, elixirs, tinctures, solutions, suspensions, syrups and emulsions, or by injection. Likewise, they may also be administered in intravenous (both bolus and infusion), intraperitoneal, subcutaneous, topical with or without occlusion, or intramuscular form, all using forms well known to those of ordinary skill in the pharmaceutical arts. An effective but non-toxic amount of the compound desired can be employed as a canine IgE modulating agent.

The daily dosage of the products may be varied over a wide range. Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

For combination treatment with more than one active agent, where the active agents are in separate dosage formulations, the active agents can be administered concurrently, or they each can be administered at separately staggered times.

The dosage regimen utilizing the compounds of the s present invention is selected in accordance with a variety of factors including type, species, age, weight, sex and medical condition of the animal, the severity of the condition to be treated, and the particular compound thereof employed. A veterinarian of ordinary skill can readily determine and prescribe the effective amount of the drug required to prevent, counter or arrest the progress of the condition. Optimal precision in achieving concentrations of drug within the range that yields efficacy without toxicity requires a regimen based on the kinetics of the drug's availability to target sites. This involves a consideration of the distribution, equilibrium, and elimination of a drug.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water mid the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methylcellulose and the like. Other dispersing agents which may be employed include glycerin and the like. For parenteral administration, sterile suspensions and solutions are desired. Isotonic preparations which generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinyl-pyrrolidone, pyran copolymer, polyhydroxypropylmethacryl-amidephenol, polyhydroxy-ethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydro-pyrans, polycyanoacrylates and cross-linked or amphipathic block copolymers of hydrogels.

The following examples illustrate the present invention without, however, limiting the same thereto.

EXAMPLE 1

Genomic Cloning

A canine liver genomic DNA bactreriophage library was purchased from Clontech Inc. and $1\times10^6$ individual plaques were screened with a 4.3 kb XhoI-EcoRI fragment containing the entire human IgA constant region gene (Kirsch et. al.) essentially as described in Hieter, P., et al., 1981, Nature. 294: 536–540 and Gazdar, A., et al., 1986, Blood. 67: 1542–1549. Filters were hybridized overnight at 42° C. in a 10% Dextran Sulfate, 4× SSC, 50% formamide, 0.8% Denhardt's Tris buffered solution. After hybridization, filters were washed with 2× SSC, 0.1% SDS at room temperature for 30 minutes, 1× SSC, 0.1% SDS at room temperature for 30 minutes and 1× SSC, 0.1% SDS at 42° C. for 30 minutes. Five positive bacteriophage were plaque purified, and large scale lysates were prepared. Restriction mapping of positive bacteriophage clones were performed according to manufacturer's suggested conditions with the restriction enzymes indicated. Regions of the clones containing the canine IgA and IgE constant region were identified using the human IgA constant region probe described above and a 2.8 kb BamHI fragment encoding the human genomic IgE constant region (Kirsch et. al.). One clone, clone 19, contained two SstI fragments, 1.2 and 1.9 kb that hybridized to the human IgE constant region probe. These fragments were excised and clone into the SstI site of Bluescript (Stratagene).

EXAMPLE 2

Nucleotide Sequence Analysis

The DNA sequence of relevant regions of the canine IgE constant region genes was determined by the "dideoxy" chain termination method using the USB Sequenase DNA sequencing kit. Synthetic oligonucleotides used as sequencing primers were synthesized on an ABI 381 synthesizer or purchased from Stratagene. Nucleic acid alignments ad translations were done using the University of Wisconsin Sequence analysis software package (Devereux, J., P. Haeverli, and O. Smithies. 1984. Nuc. Acid. Res. 12: 387–395).

EXAMPLE 3

Genomic DNA Extraction and Analysis

Genomic DNA was prepared (Basic Methods in Molecular Biology Eds. Davis, L., Dibner., M., and Battey, J. Elsevier New York 1986) from canine liver or purchased from Clontech. 10 μg of canine liver genomic DNA was digested to completion with the restriction enzymes BamHI, EcoRI, XbaI and SaiI (BMB) as specified by the supplier, fractionated on a 0.8% agarose gel, and transferred to nitrocellulose paper by the method of Southern. Canine IgE constant s region gene probes were labelled with [$^{32}$P] by nick translation and consisted of a) 1.2 kb SstI fragment containing the $CH_1$ and part of the $CH_2$ coding region, b) 300 b.p. ApaI-SstI fragment containing part of the $CH_2$ coding region, and c) a 180 b.p. XhoI-BamHI fragment containing part of the $CH_1$ coding region.

Initial genomic Southern blot analyis using both human and mouse IgE constant region probes failed to detect canine IgE constant region sequences under reduced stringency blot washing conditions. Previous work showed that IgA constant region genes are more closely conserved from species to species than IgE constant region genes, but are closely linked to the IgE sequences. Therefore, a DNA fragment containing the human IgA constant region gene was used as a probe to screen a canine genomic liver DNA bacteriophage library to isolate recombinant clones containing the canine IgA constant region gene. Five positive bacteriophage clones were identified and plaque purified. Each of these clones was probed with the human IgA and IgE constant region gene fragments and one of the clones, clone 19, was shown to have sequences that hybridized to both the human IgA and IgE constant region gene probes. This clone was further characterized.

Initial restriction mapping and Southern blot analysis suggested that the canine IgE constant region gene was encoded on two SstI fragments 1.2 and 1.9 kb in size. These restriction fragments were subcloned and detailed nucleotide sequence analyis was performed. This sequence analysis demonstrated that these two fragments contained the entire coding region of the canine IgE constant region gene and that the common SstI restriction enzyme site shared by the two fragments was contained within the CH2 coding sequence. The entire canine IgE constant region gene is encoded in four exons spread out over 2 kb.

EXAMPLE 4

Cloning of of Canine IgE For Expression of the Canine IgE Polypeptide in Other Host Cell Systems a) Cloning of Canine IgE cDNA Into a Bacterial Expression Vector Recombinant Canine IgE is produced in a bacterium such as *E.coli* following the insertion of the optimal canine IgE cDNA sequence into expression vectors designed to direct the expression of heterologous proteins. These vectors are constructed such that recombinant canine IgE is synthesized alone or as a fusion protein for subsequent manipulation. Expression may be controlled such that recombinant canine IgE is recovered as a soluble protein or within insoluble inclusion bodies. Vectors such as pBR2.22, pSKF, pUR, pATH, pGEX, pT7-5, pT7-6, pT7-7, pET, pIBI (IBI), pSP6/T7-19 (Gibco/BRL), pBluescript II (Stratagene), pTZ18R, pTZ19R (USB), pSE420 (Invitrogen) or the like are suitable for these purposes.

b) Cloning of Canine IgE cDNA Into a Yeast Expression Vector

Recombinant Canine IgE is produced in a yeast such as *Saccharomyces cerevisiae* following the insertion of the optimal canine IgE cDNA cistron into expression vectors designed to direct the intracellular or extracellular expression of heterologous proteins. In the case of intracellular expression, vectors such as EmBLyex4 or the like are ligated to the canine IgE cistron (Rinas, U. et al., Biotechnology 8: 543–545 (1990); Horowitz B. et al., J. Biol. Chem. 265: 4189–4192 (1989)). For extracellular expression, the canine IgE cistron is ligated into yeast expression vectors which fuse a secretion signal (a yeast or mammalian peptide) to the amino terminus of the canine IgE protein (Jacobson, M. A., Gene 85: 511–516 (1989); Riett L. and Bellon N. Biochem. 28: 2941–2949 (1989)).

c) Cloning of Canine IgE cDNA into a viral expression vector Recombinant canine IgE is produced in mammalian host cells, such as HeLa S3 cells, after infection with vaccinia virus containing the canine IgE cDNA sequence. To produce canine IgE:vaccinia virus, the canine IgE cDNA is first ligated into a transfer vector, such as pSC11, pTKgptF1s, pMJ601 or other suitable vector, then transferred to vaccinia virus by homologous recombination. After plaque purification and virus amplification, canine IgE:vaccinia virus is used to infect mammalian host cells and produce recombinant canine IgE protein.

EXAMPLE 5

Process for the Production of a Recombinant Canine IgE Polypeptide

Recombinant canine IgE is produced by a) transforming a host cell with DNA encoding canine IgE protein to produce a recombinant host cell;

b) culturing the recombinant host cell under conditions which allow the production of canine IgE; and c) recovering the canine IgE.

The recombinant canine IgE is purified and characterized by standard methods.

EXAMPLE 6

Compounds that modulate canine IgE activity may be detected by a variety of methods. A method of identifying compounds that affect canine I gE comprises:

(a) mixing a test compound with a solution containing canine IgE to form a mixture;

(b) measuring; canine IgE activity in the mixture; and (c) comparing the canine IgE activity of the mixture to a standard.

Compounds that modulate canine IgE activity may be formulated into pharmaceutical compositions. Such pharmaceutical compositions may be useful for treating diseases or conditions that are characterized by altered canine IgE activity. Examples of such diseases wherein the canine IgE activity is altered include allergic reactions.

EXAMPLE 7

DNA which is structurally related to DNA encoding canine IgE is detected with a probe. A suitable probe may be derived from DNA having all or a portion of the nucleotide sequence of FIG. 1, RNA encoded by DNA having all or a portion of the nucleotide sequence of FIG. 1, degenerate oligonucleotides derived from a portion of the amino acid sequence of FIG. 1 or an antibody directed against canine IgE.

EXAMPLE 8

A kit for the detection and characterization of DNA or RNA encoding canine IgE or canine IgE is prepared by conventional methods. The kit may contain DNA encoding canine IgE, recombinant canine IgE, RNA corresponding to the DNA encoding canine IgE or antibodies to canine IgE. The kit may be used to characterize test samples, such as forensic samples, taxonomic samples or epidemiological samples.

EXAMPLE 9

Use of mutagenized Canine IgE

DNA encoding Canine IgE is mutagenized using standard methods to produce an altered Canine IgE gene. Host cells are transformed with the altered Canine IgE to produce altered Canine IgE protein. The altered Canine IgE protein may be isolated, purified and used to characterize the function of Canine IgE protein.

EXAMPLE 10

Preparation of Immunogenic Compositions

Purified recombinant canine IgE are formulated according to known methods, such as by the admixture of a pharmaceutically acceptable carrier or a vaccine adjuvant. The amount of canine IgE per formulation may vary according to a variety of factors, including but not limited to the animal's condition, weight, age and sex. Such formulations are administered to an animal in amounts sufficient to induce an immune response in the animal. Administration of the recombinant canine IgE formulation may be by a variety of routes, including but not limited to oral, subcutaneous, topical, mucosal and intramuscular.

EXAMPLE 11

Preparation of Antibodies to Canine IgE

Purified recombinant canine IgE is used to generate antibodies. The term "antibody" as used herein includes both polyclonal and monoclonal antibodies as well as fragments thereof, such as Fv, Fab and F(ab)2 fragments that are capable of binding antigen or hapten. The antibodies are used in a variety of ways, including but not limited to the purification of recombinant canine IgE, the purification of native canine IgE, and kits. Kits would comprise a compartmentalized carrier suitable to hold in close confinement at least one container. The carrier would further comprise reagents such as the anti-canine IgE antibody or the recombinant canine IgE suitable for detecting canine IgE or fragments of canine IgE or antibodies to canine IgE. The carrier may also contain means for detection such as labeled antigen or enzyme substrates or the like. The antibodies or canine IgE or kits are useful for a variety of purposes, including but not limited to forensic analyses and epidemiological studies.

What is claimed is:

1. A DNA molecule having the nucleotide sequence of SEQ. ID. NO.: 1.

2. An expression vector comprising the DNA molecule of claim 1.

3. A recombinant cell transformed with the vector of claim 2.

4. A process for expression of recombinant canine immunoglobulin E, comprising culturing the cells of claim 21 under conditions which allow expression of canine immunoglobulin E.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1927 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
CAGAGCAGAT  ACCCAGGTCA  ACAGCGGGCC  TGGCATATGA  TGGGGTGACA  GTCCCCAAGG      60
CAGGCACTGA  CACTGGCCCT  GTCCCCACAG  CCACCAGCCA  GGACCTGTCT  GTGTTCCCCT     120
TGGCCTCCTG  CTGTAAAGAC  AACATCGCCA  GTACCTCTGT  TACACTGGGC  TGTCTGGTCA     180
CCGGCTATCT  CCCCATGTCG  ACAACTGTGA  CCTGGGACAC  GGGGTCTCTA  AATAAGAATG     240
TCACGACCTT  CCCCACCACC  TTCCACGAGA  CCTACGGCCT  CCACAGCATC  GTCAGCCAGG     300
TGACCGCCTC  GGGCAAGTGG  GCCAAACAGA  GGTTCACCTG  CAGCGTGGCT  CACGCTGAGT     360
CCACCGCCAT  CAACAAGACC  TTCAGTGGTA  AGCCAGGGTT  GGGCTGGCCC  ACATGACACT     420
GGAGGGAGAA  GGGACAGGCT  GGGCGGGAGT  GGTAGGAGAG  GGGTGGTGGG  CGGGCCCGAT     480
GCCGCCATGG  CTGGTAACGC  CCAGCACATG  TGGGGCTGGG  GCTGACACAT  GAGTCCCGTG     540
GGCTCAGAGA  CACCACTGCC  ACATGGCTGC  CTCTACTTCT  AGCATGTGCC  TTAAACTTCA     600
TTCCGCCTAC  CGTGAAGCTC  TTCCACTCCT  CCTGCAACCC  CGTCGGTGAT  ACCCACACCA     660
CCATCCAGCT  CCTGTGCCTC  ATCTCTGGCT  ACGTCCCAGG  TGACATGGAG  GTCATCTGGC     720
TGGTGGATGG  GCAAAAGGCT  ACAAACATAT  TCCCATACAC  TGCACCCGGC  ACAAAGGAGG     780
GCAACGTGAC  CTCTACCCAC  AGCGAGCTCA  ACATCACCCA  GGGCGAGTGG  GTATCCCAAA     840
AAACCTACAC  CTGCCAGGTC  ACCTATCAAG  GCTTTACCTT  TAAAGATGAG  GCTCGCAAGT     900
GCTCAGGTAT  GGCCCCCCTG  TCCCCAGAA  ACCCAGATGC  GCGAGGCTCA  GAGATGAGGG     960
CCAAGGCACG  CCCTCATGCA  GCCTCTCACA  CACTGCAGAG  TCCGACCCCC  GAGGCGTGAC    1020
GAGCTACCTG  AGCCCACCCA  GCCCCCTTGA  CCTGTATGTC  CACAAGGCGC  CAAGATCAC    1080
CTGCCTGGTA  GTGGACCTGG  CCACCATGGA  AGGCATGAAC  CTGACCTGGT  ACCGGGAGAG    1140
CAAAGAACCC  GTGAACCCGG  GCCCTTTGAA  CAAGAAGGAT  CACTTCAATG  GGACGATCAC    1200
AGTCACGTCT  ACCCTGCCAG  TGAACACCAA  TGACTGGATC  GAGGGCGAGA  CCTACTATTG    1260
CAGGGTGACC  CACCCGCACC  TGCCCAAGGA  CATCGTGCGC  TCCATTGCCA  AGGCCCTGG    1320
TGAGCCACGG  GCCCAGGGGA  GGTGGGCGGG  CCTCCTGAGC  CGGAGCCTGG  GCTGACCCA    1380
CACCTATCCA  CAGGCAAGCG  TGCCCCCCCG  GATGTGTACT  TGTTCCTGCC  ACCGGAGGAG    1440
GAGCAGGGGA  CCAAGGACAG  AGTCACCCTC  ACGTGCCTGA  TCCAGAACTT  CTTCCCCGCG    1500
GACATTTCAG  TGCAATGGCT  GCGAAACGAC  AGCCCCATCC  AGACAGACCA  GTACACCACC    1560
```

```
ACGGGGCCCC  ACAAGGTCTC  GGGCTCCAGG  CCTGCCTTCT  TCATCTTCAG  CCGCCTGGAG    1620

GTTAGCCGGG  TGGACTGGGA  GCAGAAAAAC  AAATTCACCT  GCCAAGTGGT  GCATGAGGCG    1680

CTGTCCGGCT  CTAGGATCCT  CCAGAAATGG  GTGTCCAAAA  CCCCGGTAA   ATGATGCCCA    1740

CCCTCCTCCC  GCCGCCACCC  CCCAGGGCTC  CACCTGCTGG  GAGGGAGGGG  GGCTGGCAAG    1800

ACCCTCCATC  TGTCCTTGTC  AATAAACACT  CCAGTGTCTG  CTTGGAGCCC  TGGGCACACC    1860

CATTTCTTGG  GGGTGGGCAG  GGTTGCAGAG  CAGGGATGTC  TTGGCACAGA  AGGGTCCCCC    1920

AGGGTGT                                                                  1927
```

( 2 ) INFORMATION FOR SEQ ID NO:2:

( i ) SEQUENCE CHARACTERISTICS:
        ( A ) LENGTH: 426 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Thr  Ser  Gln  Asp  Leu  Ser  Val  Phe  Pro  Leu  Ala  Ser  Cys  Cys  Lys  Asp
 1              5                        10                       15

Asn  Ile  Ala  Ser  Thr  Ser  Val  Thr  Leu  Gly  Cys  Leu  Val  Thr  Gly  Tyr
              20                        25                       30

Leu  Pro  Met  Ser  Thr  Thr  Val  Thr  Trp  Asp  Thr  Gly  Ser  Leu  Asn  Lys
              35                        40                       45

Asn  Val  Thr  Thr  Phe  Pro  Thr  Thr  Phe  His  Glu  Thr  Tyr  Gly  Leu  His
     50                        55                       60

Ser  Ile  Val  Ser  Gln  Val  Thr  Ala  Ser  Gly  Lys  Trp  Ala  Lys  Gln  Arg
65                        70                       75                       80

Phe  Thr  Cys  Ser  Val  Ala  His  Ala  Glu  Ser  Thr  Ala  Ile  Asn  Lys  Thr
                    85                        90                       95

Phe  Ser  Ala  Cys  Ala  Leu  Asn  Phe  Ile  Pro  Pro  Thr  Val  Lys  Leu  Phe
                   100                       105                      110

His  Ser  Ser  Cys  Asn  Pro  Val  Gly  Asp  Thr  His  Thr  Thr  Ile  Gln  Leu
               115                       120                      125

Leu  Cys  Leu  Ile  Ser  Gly  Tyr  Val  Pro  Gly  Asp  Met  Glu  Val  Ile  Trp
     130                       135                      140

Leu  Val  Asp  Gly  Gln  Lys  Ala  Thr  Asn  Ile  Phe  Pro  Tyr  Thr  Ala  Pro
145                       150                       155                     160

Gly  Thr  Lys  Glu  Gly  Asn  Val  Thr  Ser  Thr  His  Ser  Glu  Leu  Asn  Ile
               165                       170                      175

Thr  Gln  Gly  Glu  Trp  Val  Ser  Gln  Lys  Thr  Tyr  Thr  Cys  Gln  Val  Thr
               180                       185                      190

Tyr  Gln  Gly  Phe  Thr  Phe  Lys  Asp  Glu  Ala  Arg  Lys  Cys  Ser  Glu  Ser
               195                       200                      205

Asp  Pro  Arg  Gly  Val  Thr  Ser  Tyr  Leu  Ser  Pro  Pro  Ser  Pro  Leu  Asp
          210                       215                      220

Leu  Tyr  Val  His  Lys  Ala  Pro  Lys  Ile  Thr  Cys  Leu  Val  Val  Asp  Leu
225                       230                       235                     240

Ala  Thr  Met  Glu  Gly  Met  Asn  Leu  Thr  Trp  Tyr  Arg  Glu  Ser  Lys  Glu
               245                       250                      255

Pro  Val  Asn  Pro  Gly  Pro  Leu  Asn  Lys  Lys  Asp  His  Phe  Asn  Gly  Thr
               260                       265                      270

Ile  Thr  Val  Thr  Ser  Thr  Leu  Pro  Val  Asn  Thr  Asn  Asp  Trp  Ile  Glu
          275                       280                      285
```

| | | | | | | | | | | | | | | |
|---|---|---|---|---|---|---|---|---|---|---|---|---|---|---|
| Gly | Glu 290 | Thr | Tyr | Tyr | Cys | Arg 295 | Val | Thr | His | Pro | His 300 | Leu | Pro | Lys | Asp |
| Ile 305 | Val | Arg | Ser | Ile | Ala 310 | Lys | Ala | Pro | Gly | Lys 315 | Arg | Ala | Pro | Pro | Asp 320 |
| Val | Tyr | Leu | Phe | Leu 325 | Pro | Pro | Glu | Glu | Glu 330 | Gln | Gly | Thr | Lys | Asp 335 | Arg |
| Val | Thr | Leu | Thr 340 | Cys | Leu | Ile | Gln | Asn 345 | Phe | Phe | Pro | Ala | Asp 350 | Ile | Ser |
| Val | Gln | Trp 355 | Leu | Arg | Asn | Asp | Ser 360 | Pro | Ile | Gln | Thr | Asp 365 | Gln | Tyr | Thr |
| Thr | Thr 370 | Gly | Pro | His | Lys | Val 375 | Ser | Gly | Ser | Arg | Pro 380 | Ala | Phe | Phe | Ile |
| Phe 385 | Ser | Arg | Leu | Glu | Val 390 | Ser | Arg | Val | Asp | Trp 395 | Glu | Gln | Lys | Asn | Lys 400 |
| Phe | Thr | Cys | Gln | Val 405 | Val | His | Glu | Ala | Leu 410 | Ser | Gly | Ser | Arg | Ile 415 | Leu |
| Gln | Lys | Trp | Val 420 | Ser | Lys | Thr | Pro | Gly 425 | Lys | | | | | | |